United States Patent [19]

Archer, III

[11] Patent Number: 5,586,561

[45] Date of Patent: Dec. 24, 1996

[54] BACK GUARD WITH TUNNEL FOR SPINAL COLUMN

[75] Inventor: Shreve M. Archer, III, Carmel Valley, Calif.

[73] Assignee: Entropy Racing, Inc., Monterey, Calif.

[21] Appl. No.: 301,891

[22] Filed: Sep. 7, 1994

Related U.S. Application Data

[63] Continuation-in-part of Ser. No. 163,906, Dec. 6, 1993, Pat. No. 5,400,801.

[51] Int. Cl.$^6$ ............................................. A61F 5/37
[52] U.S. Cl. ............................................. 128/846; 602/19
[58] Field of Search .............................. 128/845, 846, 128/102.1, 103.1, 104.1, 107.1, 874, 876; 2/2, 16, 44, 92; 606/69–71; 602/5, 19

[56] References Cited

U.S. PATENT DOCUMENTS

| | | |
|---|---|---|
| 1,585,341 | 5/1926 | Foulke ................................. 602/19 |
| 4,541,419 | 9/1985 | Osawa ................................. 602/19 |
| 5,140,995 | 8/1992 | Uhl ..................................... 128/846 |
| 5,328,447 | 7/1994 | Kapounek ............................ 602/19 |

FOREIGN PATENT DOCUMENTS 4117768 12/1992 Germany ............................ 602/19

*Primary Examiner*—Max Hindenburg
*Assistant Examiner*—Pamela Wingood
*Attorney, Agent, or Firm*—LaRiviere, Grubman & Payne

[57] ABSTRACT

A back guard is provided for protecting the back against impact. The back guard is worn by a wearer over the back. The guard comprises interlocked members. Each of the members is curved to conform to the spine. In particular, a recess is provided for the spinous process to prevent impact thereto during a collision.

8 Claims, 15 Drawing Sheets

BACK GUARD WITH TUNNEL FOR SPINAL COLUMN

This is a continuation-in-part of application Ser. No. 08/163,906, filed Dec. 6, 1993, now U.S. Pat. No. 5,400,801.

TECHNICAL FIELD

The invention relates to protective clothing. More specifically, the invention relates to back guards for preventing to mitigating injury due to impact.

BACKGROUND ART

In order to understand the design of a safety system based on a medical model, an understanding of human anatomy and the mechanisms of injury thereto is necessary.

Referring to FIG. 1, a lateral side elevation view of human spine 10 is shown. The spine is a flexible and flexious column made up of a series of bones called vertebrae. Each person typically has 33 vertebrae. These are broken up into five types according to position. They are: cervical, dorsal ("thoracic"), lumbar, sacral, and coccygeal. There are typically 7 cervical vertebrae (C1–C7), 12 thoracic vertebrae (D1–D12), five lumbar vertebrae (L1–L5), five sacral vertebrae, and four coccygeal vertebrae. As is known, in adulthood, the sacral and coccygeal regions generally unite to form two bones, namely, the sacrum 1 and coccyx 2. The other vertebrae generally stay separate.

Each vertebra consists of two essential parts, namely, an anterior solid segment ("body") and a posterior segment ("arch"). The arch is formed of two pedicle and two laminae, which support seven processes, namely, four articular, two transverse and one spinous.

Referring to FIG. 2, a top elevation view of seventh cervical vertebra C7 is shown. As can be seen, laminae 3 are two broad plates of bone which complete a neural arch by fusing together. Laminae 3 enclose and define spinal foramen 5. Spinal foramen 5 serves for protection of the spinal cord. Spinous process 4 projects backward from the junction of laminae 3, and serves for attachment of muscles and ligaments. The distinctive character of seventh cervical vertebra C7 is the existence of a long and prominent spinous process 4. For this reason, seventh cervical vertebrae C7 is often referred to as "vertebrae prominent."

Referring to FIG. 3, a lateral elevation view of thoracic vertebra 30 is shown. As can be seen, each lamina 3 is broad, thick and imbricated. For thoracic vertebra 30, spinal foramen 5 is small and of a circular form (not shown). Spinous process 4 for thoracic vertebrae are long, triangular on transverse section, directed obliquely downward and terminate in a tubercular extremity.

Referring to FIG. 4, a top elevation view of lumbar vertebra 40 is shown. As can be seen, each lamina 3 is broad and short, and spinal foramen 5 is triangular. Spinous process 4 is thick and broad.

As can be seen from FIG. 1, spinous processes 4 is prominent, especially from seventh cervical vertebra C7 down to fifth lumbar vertebra L5. In referring to the "back", it should be understood that any and all thoracic and lumbar vertebrae are included, as well as, seventh cervical vertebra C7.

Because spinous process 4 has very little tissue between it and the exterior surface of skin of the back, its prominent extension often acts as a pile for driving into the back causing fracturing, compression or dislocation of vertebra. If a vertebra is displaced, it may pinch to sever the spinal cord.

Numerous types of injury may occur to the back. With regard to the present invention, there are several types of back injuries of which the mechanics and biomechanics will be examined.

The mechanisms of injury to the back may be thought of in three basic ways: compression, flexion-extension, and direct trauma.

Compression occurs when a load is applied in-line with the vertebral column. For example, as shown in FIG. 1, a force 16 applied in-line to spine 10 will cause compression injury. Injury to vertebrae of spine 10 depends on the relative position of the spine during impact. If spine 10 is bent in flexion, as shown in FIG. 23, the load is mostly carried by the vertebral body (e.g., body 17 as shown in FIGS. 2–4). As a result, a compression fracture 201 occurs as shown in FIG. 23. Because the vertebral ligaments remain in tact, damage to spinal cord 10 with resulting nerve injury is rare. An exception to this rarity occurs when the impact results in extrusion of the vertebral discs into the spinal canal. In that case, spinal cord compression occurs and nerve damage is typical.

If spine 10 is bent, as shown in FIG. 24, compressing load 16 is carried by facets 202 and spinous processes 4. In the case where the spine is bent and extended, disruption of the ligaments is more likely to result. This produces an unstable situation leading to spinal cord 10 compression and resulting nerve damage. In addition, if vertebral body 17 is crushed, its posterior part is more likely to be affected causing fracture 203. Fragments from fracture 203 are likely to enter the spinal canal. These fragments often cause compression of the spinal cord resulting in nerve damage.

The second type of mechanism of injury to the back is due to flexion-extension. Flexion-extension injuries, as shown in FIG. 25, often are a result of automobile accidents. This is because the occupant is restrained by a seat belt. A traction force 18 applied along spinal column 10 causes posterior ligaments 204 to be stretched. Traction force 18 also may cause parts of the vertebral arch to fracture and separate 205, as shown in FIG. 26. Besides spinal cord damage due to stretching, the spinal cord may also be damaged due to misalignment of vertebrae 20, as shown in FIG. 27. Misalignment 206 causes fracturing of vertebrae, as well as, spinal cord damage.

Injury from extension alone, as shown in FIG. 28, are uncommon. The main reason is the anterior vertebral ligaments 210 are strong. The combined structure of facets 202 and spinous process 4 resists rotation. Thus, the combination of ligament strength and rotation resistance prevents many injuries. However, when extension is combined with compression or direct impact, devastating injury may result. Typically, the vertebral arch and ligaments fail, causing the spinal cord to be directly impacted. Bleeding in the spinal cord typically results. As the spinal cord is contained within the spinal foreman 5, swelling results in cord compression. The result in lack of blood flow due to swelling causes nerve damage.

The third mechanism of injury to the back is direct trauma. Forces applied directly and transverse to the vertebral column may have two important consequences: first intervertebral ligaments, as well as the entire vertebrae itself, may fail allowing lateral displacement and cord compression or shearing; and second, failure of the vertebral arch and spinal cord impact resulting in bleeding into the spinal cord causes swelling in a confined space resulting in interruption of blood flow to the nerves and resulting in damage.

Motorcyclists are typically most vulnerable to compression, extension and direct impact injuries. Flexion and traction injuries are not as often encountered, as with automobile occupants, because a motorcyclist's lower body is not restrained by a seat belt.

While compression forces are difficult to prevent without a rigid structure between the skull and pelvis, their impact may be diminished by preventing extension, so that the load is carried by the anterior part of the vertebral bodies.

Extension should also be limited or prevented because, if the spinal column is in an extended position, direct transverse forces are more likely to cause damage to the spinal cord.

The impact of direct transverse forces may be diminished by spreading the load over a larger area and by directing it away from the spinous process.

Referring to FIG. 5, a top broken out cross section view of the back is shown. Many anatomical details have been omitted in order to avoid confusion. As shown, vertebra 20 comprises two lamina 3, spinous process 4 and spinal foramen 5. Disposed in spinal foramen 5 is spinal cord 6. As shown, ribs 13 and muscles 12 are covered by skin 11.

A first biomechanism of injury to the back is shown in FIG. 6. The injury is caused by impact to the back, and in particular, spinous process 4. Because spinous process 4 protrudes so significantly, it is a likely target for receiving a force of impact to the back, as shown by reference as force 14. Moreover, because there is so little tissue protecting tip 8 of spinous process 4, there is little protection against direct impact to spinous process 4.

As shown in FIG. 6, impact to spinous process 4 often causes vertebra 20 to break at each lamina 3. It is common for lamina 3 to break as shown during severe impact to spinous process 4. This causes spinous process 4 to be pushed into spinal cord 6.

Because spinal cord 6 is contained within a solid bony compartment, spinal foramen 5, it is compressed when spinous process 4 is pushed into spinal cord 6. Thus, the blood supply to the nerves inside spinal cord 6 is typically cut-off. This results in further injury to the individual. Unfortunately, much of this type of injury is permanent. Not only may the blood supply be cut-off, tissue and nerve damage may occur due to the impact on spinal 6 cord from spinous process 4.

In a second biomechanism of injury to the back, laminae 3 does not break, but rather the arch breaks at locations 303, namely, where the arch attaches to body 17 of vertebra 20. In this type of injury, the spinal cord is often compressed, as the arch is pushed down against body 17 causing compression of vertebra 20.

A third biomechanism of injury to the back is shown in FIG. 7. As shown, force 15 is supplied laterally against the back and, in particular, spinous process 4. This causes each lamina 3 to break. The break and pressure exerted by force 15 causes spinous process 4 to be pushed against spinal cord 6. Again, as spinal cord 6 has no where to go due to its containment within spinal foramen 5, damage to nerves and tissue of spinal cord 6 may occur, as well as, cut-off of blood supply.

To protect the back against injury, devices have been devised. In fact, most groups that organize motorcycle races require back guards. Presently, two types of back guard are typically employed.

A first type of back guard 23 is shown in FIG. 8. Back guard 23 comprises pad 21 and attach thereto plastic sheet 22. Pad 21 is typically made of foam or cloth, or a combination of both. While back guard 23 does provide some protection, it is not contoured for the spine. Therefore, no relief is provided for spinous process 4. During impact to the back, forces are still directly transferred to spinous process 4, albeit through back guard 23. Thus, little of the force of impact is transmitted to surrounding tissue and anatomical structures. Damage to the surrounding tissue and anatomical structures is typically less severe.

Also, sheet 22 is made of a flexible material. This is to allow normal flexing of a wearer's spine. Flexible materials tend to distort and deform under loading. Thus, forces are not dispersed, as much as would be desired, away from spine 10.

Moreover, due to the flexible nature of plastic sheet 22, an impact to the side of the back may also be transmitted to vertebral process 4. Thus, for example, force 24 may be transmitted along plastic sheet 22 down and up against vertebral process 4. Had sheet 22 been omitted, transmission of force 24 to vertebral process 4 may not have occurred. Rather, force 24 would be direct against muscle tissue 12 and ribs 13, which damage thereto is typically less severe. Thus, back guard 23 may cause injury, which may not have occurred with omission of back guard 23.

A second type of back guard is shown in FIGS. 9-11.

In FIG. 9, back guard 25 comprises plastic sheet 22 and pad 21. However, plastic sheet 22 of back guard 25 is contoured to provide cavity 27. Cavity 27 has a maximum height of approximately 1 cm and an opening width of approximately 8 cm.

A top elevation view of back guard 25 is shown in FIG. 10. As shown, back guard 25 comprises straps 26 attached to pad 21. Also attached to pad 21 are a plurality of plastic sheets 22. Plastic sheets 22 are typically attached to pad 21 by rivets. Plastic sheets 22 are over laid as to form a series for protecting the back. As shown by dash line 31, the tail portion 32 (shown in FIG. 11) of plastic sheet 22 fits in cavity 27 as provided by contour 33, as shown in FIG. 11.

FIG. 11 shows the underside of plastic sheet 22, absent rivets. As shown, plastic sheet 22 has contour 33 for providing cavity 27. Additionally, tail 32 is used for under laying with another plastic sheet 22.

Unfortunately, because tail 32 is located in cavity 27, the amount of relief for spinous process 4 is reduced. At some locations in cavity 27, no relief is provided due to over laying of plastic sheets 22. In fact, at some locations within cavity 27 where plastic sheets have been over laid, no relief in either the vertical or horizontal direction is provided for spinous process 4. Thus, the same problems associated with back guard 23 are also present with back guard 25. Moreover, any amount of relief provided by cavity 27 is insufficient to protect spinous process 4 from severe impact.

Another problem with back guard 25 is illustrated in FIG. 12. In FIG. 12, if spine 10 is bent in a backward direction 41, then back guard 25 will also flex in backward direction 41. Because back guard 25 is not interlocked, but over laid, there is no mechanism to prevent tail 32 from articulating into spine 10 when being flexed in backward direction 41, as shown with reference to a portion of back guard 25 in FIG. 12. Tail 32 may be pushed up against spinous process 4 causing some of the injuries described above. Thus, the force of impact may be directed to a small area on spine 10, namely, focusing force to edge 34 and against spine 10. Moreover, force from tail 32 against spinous process 4 may cause: spinous process 4 to break-off from vertebra 20, vertebral displacement of vertebra 20, or fracture of vertebra

20. An injury which may not have occurred with the omission of back guard 25. Additionally, because plastic sheets 22 of back guard 25 are not interlocked, there is no mechanism for preventing hyperextension of spine 10.

DISCLOSURE OF INVENTION

The present invention provides a back guard. The back guard is for use by a wearer to reduce the risk of injury to vertebra of the back due to impact. Thus, the present invention is for prevention to mitigation of injury caused by impact to the back of a wearer.

The back guard of the present invention is designed for attachment to the torso of an individual. The back guard should follow the spinal column of the individual. The back guard is designed to prevent breakage of vertebra of the back due to impact. The present invention is directed to preventing to mitigating vertebral displacement and fracture by avoiding to reducing loading to vertebra of spine 10. In particular, because spinous processes 4 are prominent, they are likely loaded during impact to the back. This typically causes vertebral displacement and fracture. Thus, the present invention is directed to avoid loading of spinous process 4.

Each apex of each inner contour of each guard member for covering a spinous process must be wide enough that a side impact will not normally put pressure on the spinous process. Additionally, it should be high enough such that a spinous process will not be impacted due to a direct impact to the back, absent deformation of the back guard.

By providing a recess contour for accommodating each spinous process of the spinal column of the back, each spinous process may be covered against impact by a hard material for shielding without direct impact to the spinous process. Direct impact sustained to the back often causes the spinous process to be damaged. Moreover, the inner contour of the back guard of the present invention also provides a width for lateral movement. This width allows the back guard to be misaligned and still provide sufficient recess to protect the spinous process from impact. If the back guard is shifted during impact or misaligned due to improper use, the width of the inner contour provides and extended channel for protection of the spinous process.

It should be understood that individuals are physically different. Therefore, the back guard according to the present invention may include wide tolerances to allow adaptation to different physical proportions. Thus, vertical height and horizontal width of the inner contour of the back guard may be adapted to different physical proportions. However, a 5 cm vertical height is sufficient for most people. Also, the back guard according to the present invention, in the preferred embodiment, comprises sufficient back guard members interlocked to cover from the 7th cervical vertebra down to the 5th lumbar vertebra. However, fewer or more vertebra may be covered with altering embodiments.

Each back guard member is interlocked. This is to limit the amount of forward and backward flexion of the back guard according to the present invention. While the back guard according to the present invention has sufficient tolerance between post and holes for interlocking to allow normal flexion, it may restrain the back from movement causing severe back strain to hyperextension. The amount of flexibility of each individuals back will vary from person to person. Some people will need much more rigid form of back guard, while others will be able to have one which allows for more mobility. Therefore, the back guard according to the present invention provides for a wide variety of angular articulations of the back. It should be understood that the interlocking nature of the guard members of the present invention allow the load due to impact to the back of the wearer to be distributed among the neighboring pieces or members.

Another goal of the present invention is to protect the spine by transmitting loads to surrounding structures to disburse loading. This is to prevent injury to the back, while possibly causing injury to surrounding anatomical structures and tissue.

Still another goal of the present invention is to protect the spine by providing a continuous tunnel capable of receiving heights of spinous processes. To maintain the integrity of the continuous tunnel owing to impact, the present invention provides directly connecting protective plates one to another. This direct connection of plates one to another may be accomplished by mechanical means, including but not limited to post and holes, and straps as disclosed elsewhere herein.

In particular, by directing the load due to impact away from the spinous processes, the risk of injury to the spine is reduced. There is a relative trade-off, namely, that risk of injury to the spine is reduced, and risk of injury to surrounding tissue and anatomical structure is increased by dispersally distributing the load. However, because the muscle tissue and ribs propose less devastating types of injuries when harmed, as compared to a spinal injury, the present invention realizes this as a cost-benefit effective trade-off. Moreover, by distributing the impact to a wide area, the load to any one part of the body is reduce. Thus, the degree of likelihood of severe injury is also reduced.

The present invention comprises a curved shape and interlocking plates. These features mitigate against extension injuries. For example, the back is in extension when a load is applied to the middle of spine 10. As the curve shape of the present invention provides a recess for spinous processes 4, forces are directed away from spine 10. Thus, extension of spine 10 is less likely. Also, because the present invention provides interlocked plates, forces are dispersed away from spine 10. Interlocking plates also may limit extension of spine 10 by resisting traction forces directed approximately parallel to portions of spine 10.

The present invention may be used by anybody wishing protection for their back. However, the present invention is particularly directed to users of motorcycles. It should be understood, however, that the same invention may be used in a wide variety of applications, including sports, recreational vehicle use, or every day wear. The latter being directed to individuals who have increased risk to their back due to injury or to impact, e.g. individuals with forms of osteoporosis, prior spinal damage, or some other aliment affecting the back.

The back guard according to the present invention may also be made integral to a wearer's garment.

In an embodiment of the present invention, plates forming the back guard are hinged together with a combination of straps. The straps are attached to adjacent plates for allowing forward flexion while limiting backward flexion. Also, the straps bind the plates together.

Other features of the present invention are disclosed or apparent in the section entitled "BEST MODE FOR CARRYING OUT THE INVENTION".

BRIEF DESCRIPTION OF DRAWINGS

For fuller understanding of the present invention, reference is made to the accompanying drawing in the following detailed description of the Best Mode for Carrying Out the Invention. In the drawing.

Figure 1:
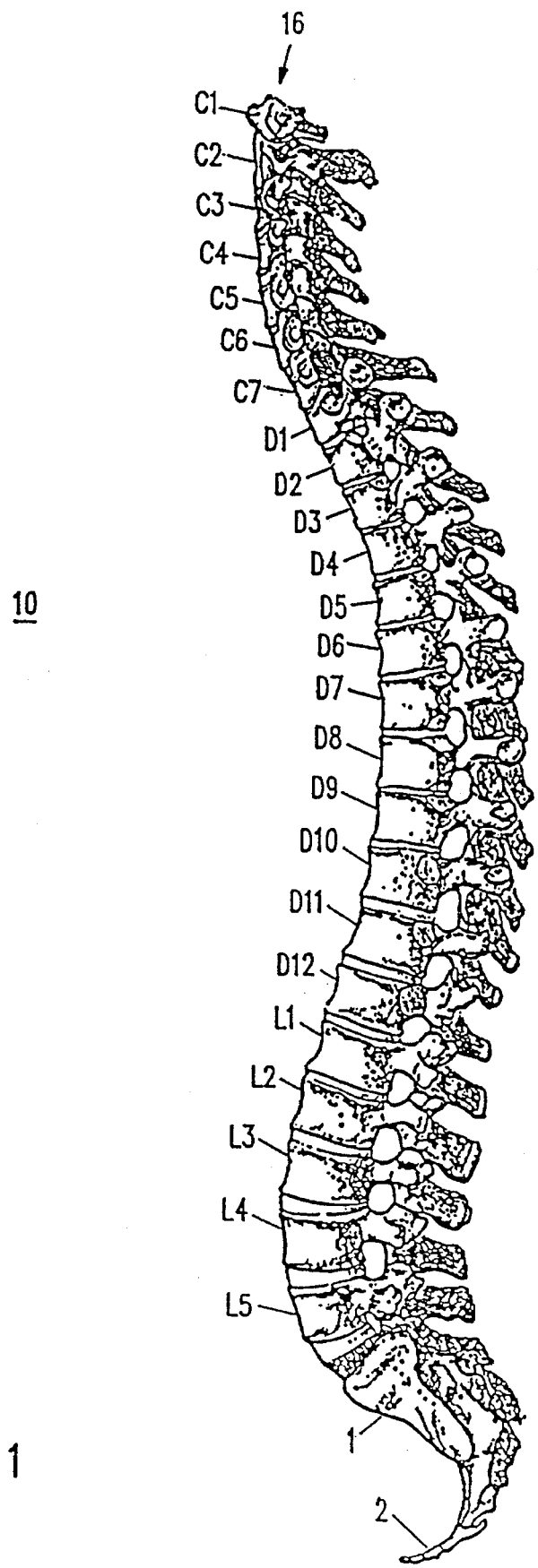
FIG. 1 illustrates a lateral elevation view of a human spine.
Figure 2:
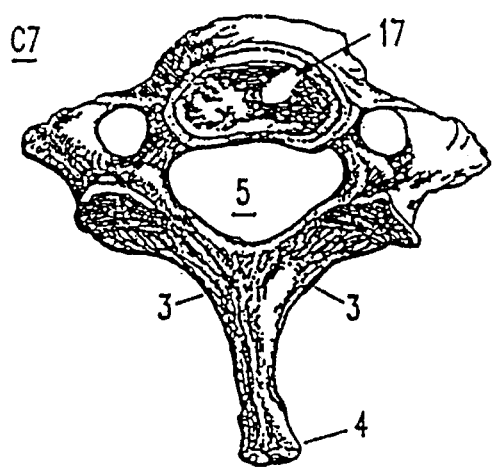
FIG. 2 illustrates a top elevation view of a seventh cervical vertebra.
Figure 3:
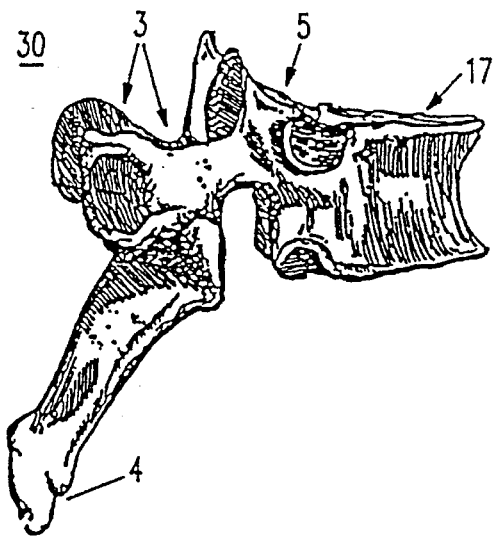
FIG. 3 illustrates a side elevation view of a thoracic vertebra.
Figure 4:
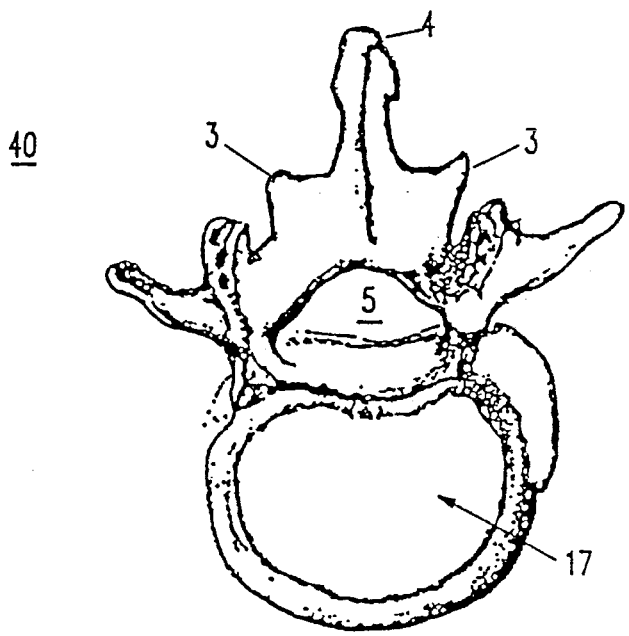
FIG. 4 illustrates a top elevation view of a lumbar vertebra.
Figure 5:
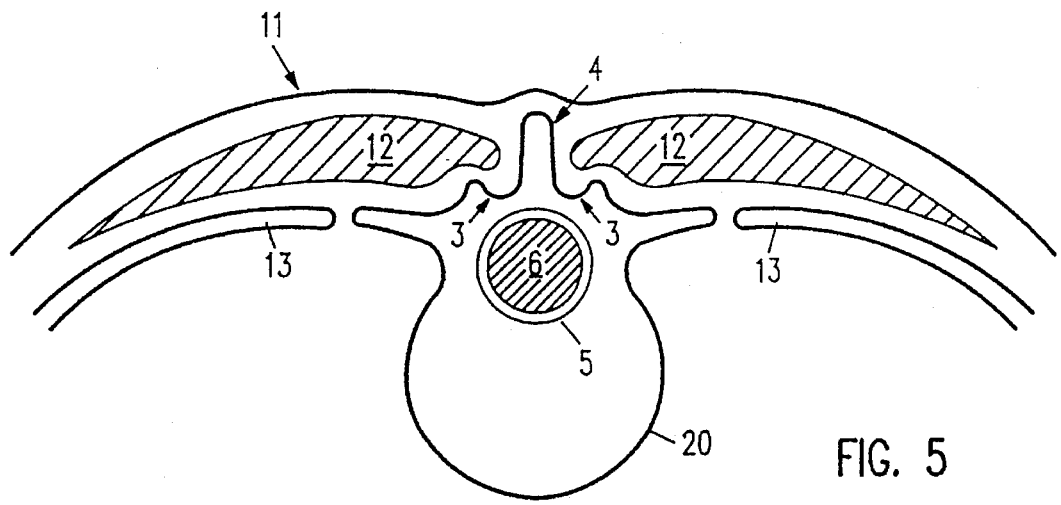
FIG. 5 is a diagram illustrating a cross-sectional view of a human vertebra and surrounding anatomical structure and tissue.
Figure 6:
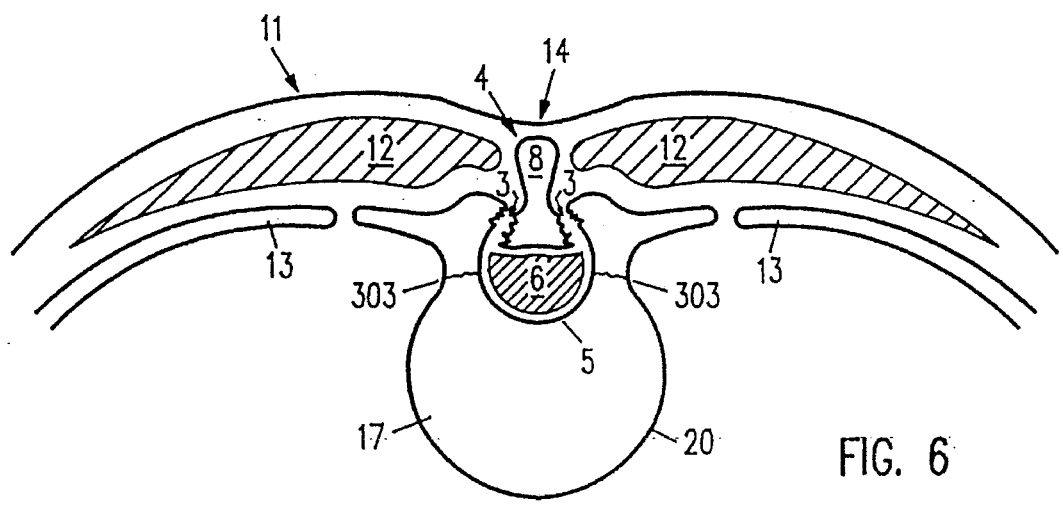
FIGS. 6–7 illustrates biomechanisms of injury to the spine and spinal cord.
Figure 7:
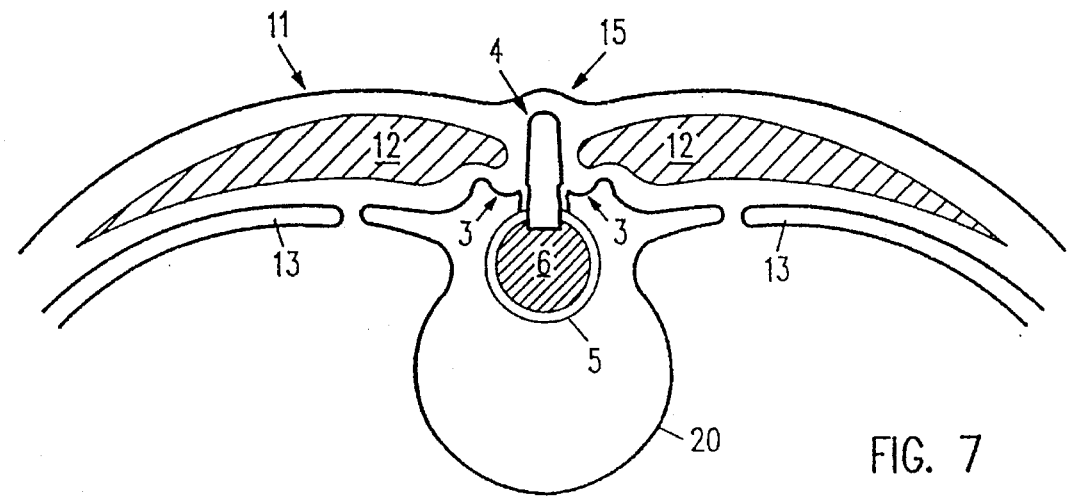
Figure 8:
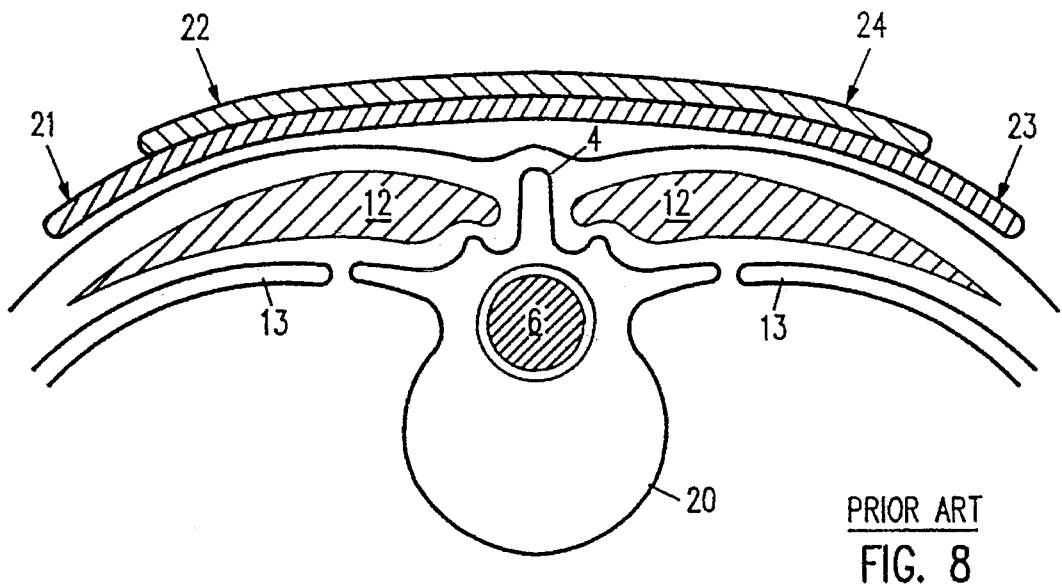
FIGS. 8–9 illustrates use of prior art back guards.
Figure 9:
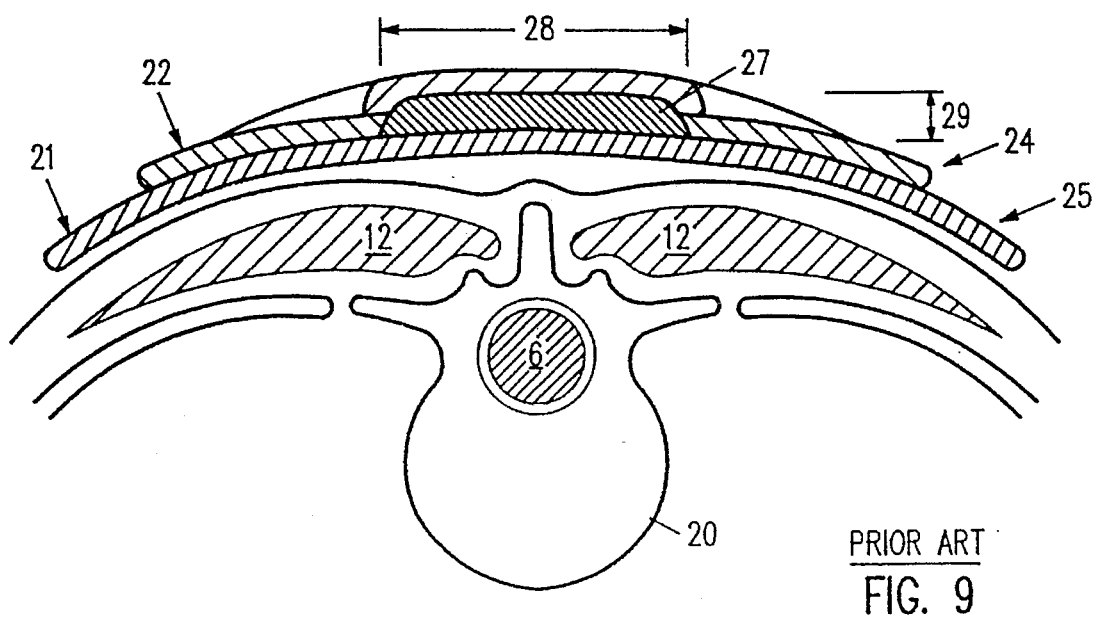
Figure 10:
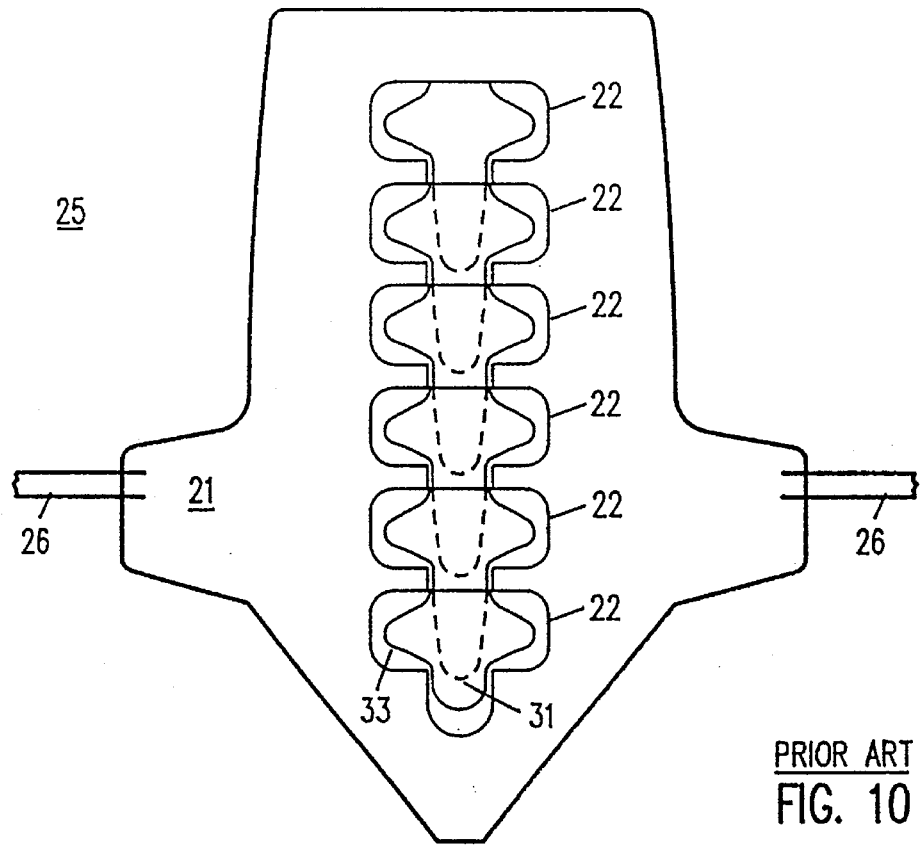
FIGS. 10–11 illustrates the prior art back guard of FIG. 9.
Figure 11:
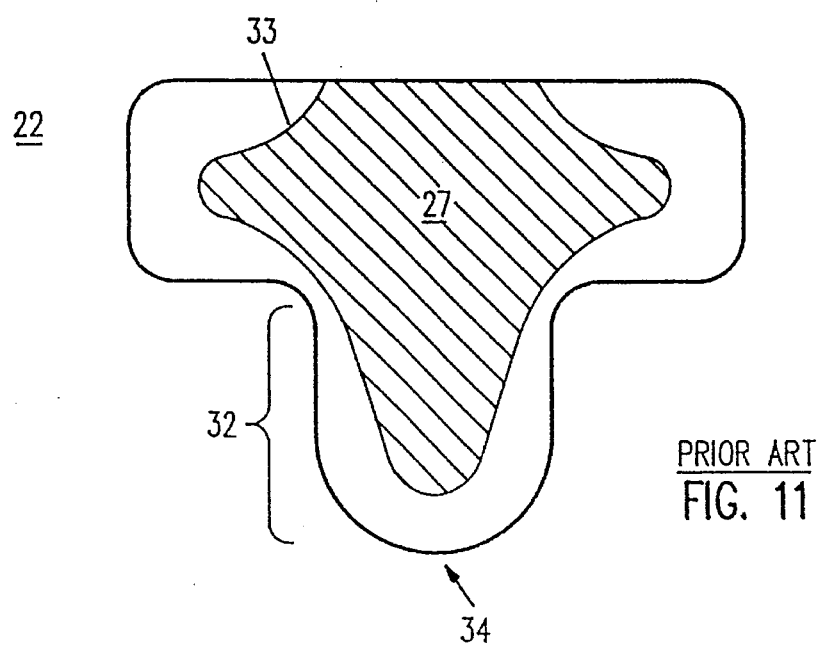
Figure 12:
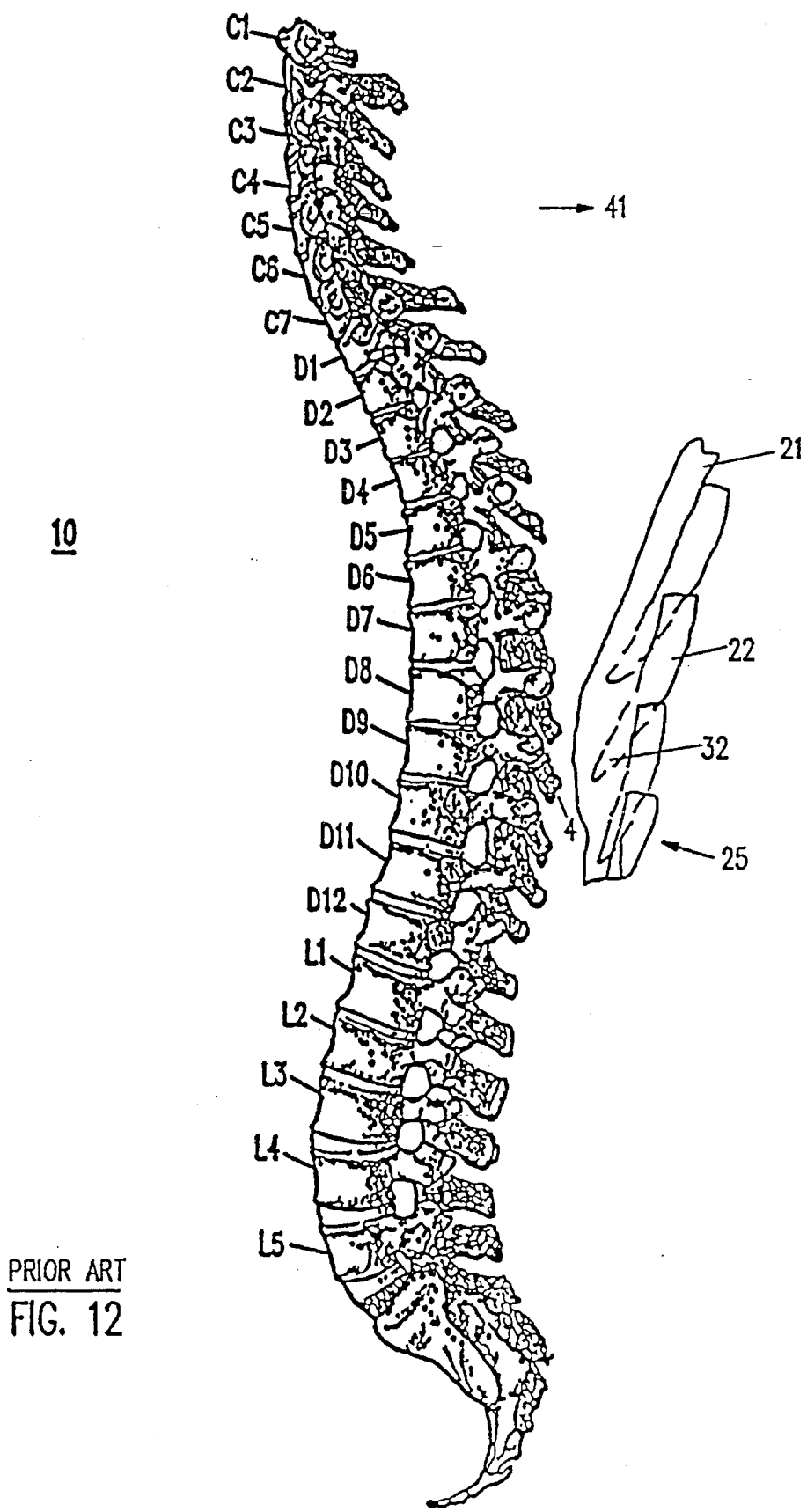
FIG. 12 illustrates use of the prior art back guard of FIG. 9.

Reference numbers refer to the same or equivalent pans of the present invention throughout the several figures of the drawing.

BEST MODE FOR CARRYING OUT THE INVENTION

Figure 13:
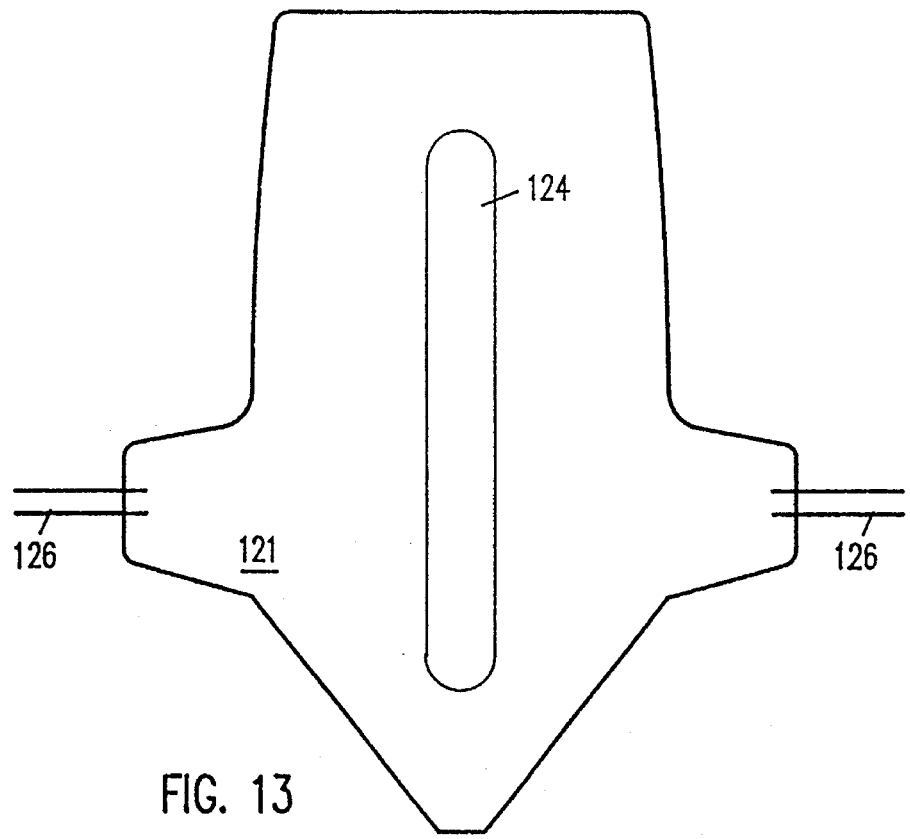
FIG. 13 illustrates a top elevation view of a back guard pad according to the present invention.

Referring to FIG. 13, pad 121, according to the present invention, is shown. Pad 121 may comprise straps 126 for attaching to the wearer. Pad 121 may comprise cloth, foam padding, or a combination of both. A tough cloth made of kevlar is preferred. In the preferred embodiment of the present invention, a channel 124 is provided in pad 121. Channel 124 is centered to pad 121. Channel 124 is to follow the series of spinous processes 4 of the back of the wearer. Use of channel 124 is explained in more detail below.

Figure 14:
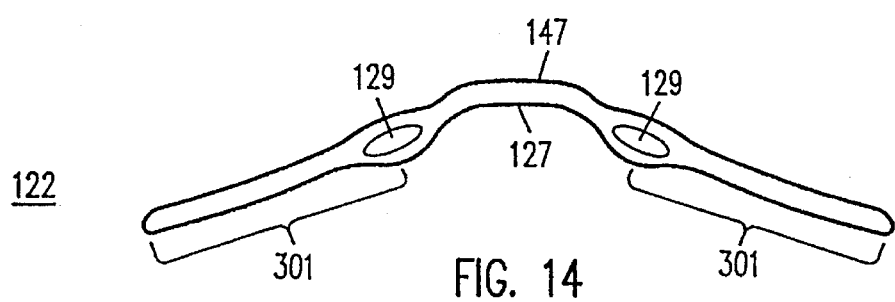
FIG. 14 illustrates a side elevation view of a back guard member according to the present invention.

Referring to FIG. 14, a front view of a back guard member 122 is shown. Back guard member 122 (or plate) comprises inner contour 127 and outer contour 147. Back guard 122 also comprises holes 129 as will be explained.

Back guard member 122 may be made of a hard plastic material. Back guard member 122 may be made of a carbon fiber or kevlar material. Back guard members 122 are rigid to effectively transmit loading to a large area, i.e., dispersing the load. Also, the material used for back guard member 122 is resistant to stretching. This mitigates against extension, as well as, deformation of the plates.

Figure 15:
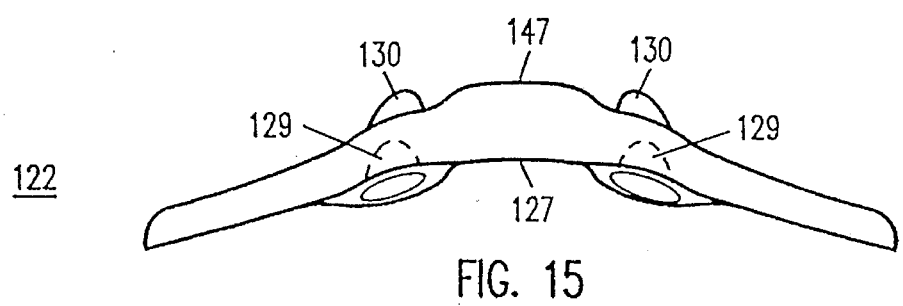
FIG. 15 is a top front perspective view of the back guard member of FIG. 14.

Referring to FIG. 15, a front perspective view of member 122 is shown. As can be seen, holes 129 extend into member 122. Thus, member 122 defines each cavity for holes 129. Member 122 also comprises interlocking posts 130.

Figure 29:
FIG. 29 is a cross-sectional view illustrating an alternate embodiment for interlocking in accordance with the present invention.

Referring to FIG. 29, posts 130 and holes 129 may be curved toward the back. This may allow for more forward flexion, while limiting backward flexion. By allowing flexion in this manner, edges 301 of back guard members 122 do not apply pressure on spine 10.

Figure 16:
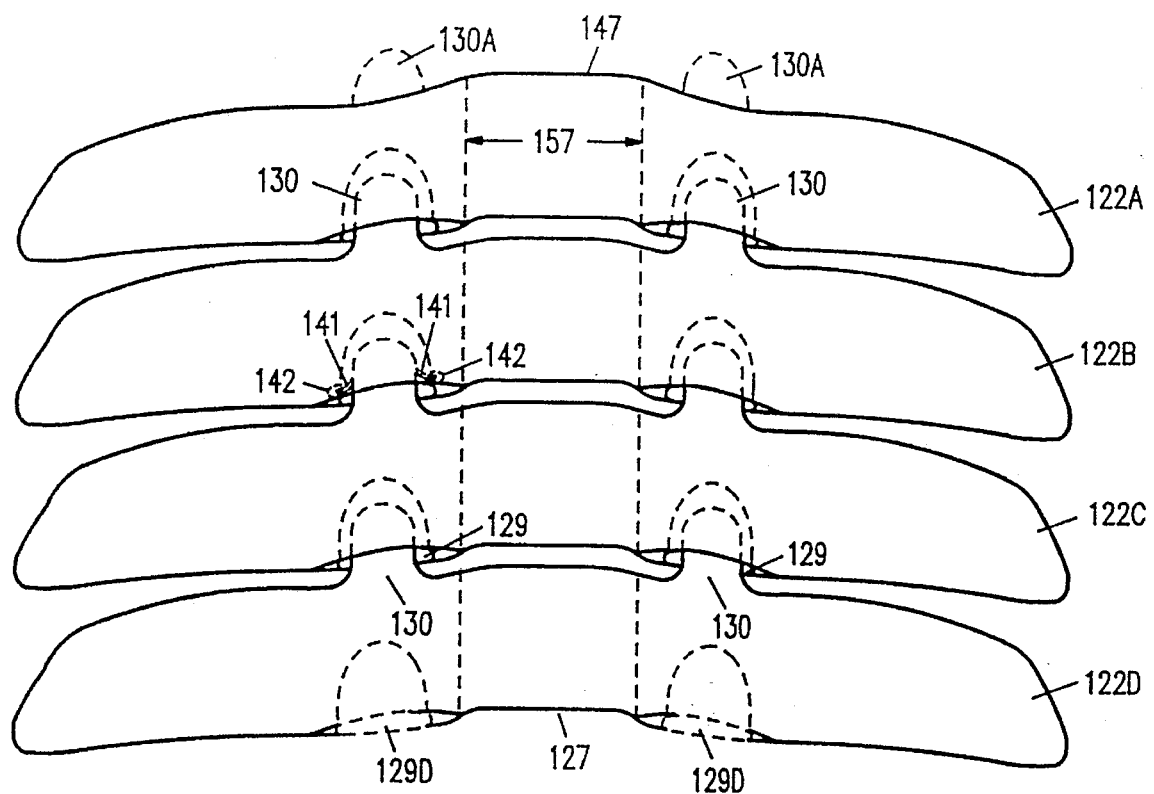
FIG. 16 illustrates a top elevation view of a plurality of interlocked back guard members according to the present invention.

Referring to FIG. 16, a plurality of back guard members 122A–D are shown. As shown, holes 129 extend into members 122A–D. Holes 129 are for receiving posts 130. Additionally, holes 129 may optionally include recesses 142. Additionally, post 130 may then optionally include tabs 141. Tabs 141 are for mating with recesses 142. In this manner, back guard member 122C may be snapped into place for interlocking with back guard 122B as shown. However, it should be understood that interlocking occurs with the mating of posts 130 to holes 129. As members 122 are attached to pad 121, no additional locking mechanism for posts 130 to holes 129 is needed.

It should be understood that in order to maintain the integrity of a continuous tunnel as provided in accordance with the present invention, it is necessary that back guard members 122A–D be directly connected to one another. As described herein, post and holes may be used as a mechanical means for connecting back guard members 122A–D directly one to another; however, it should be appreciated that other types of direct mechanical attachment may be used.

Because back guard members 122 are interlocked, as described, load applied to one of the plurality of back guard members 122 is also transferred to a neighboring back guard member. In this manner, loading may be transferred to a plurality of back guard members 122 for more dispersion of loading forces. Thus, forces may be transmitted away from spine 10.

While only two posts and holes are shown, fewer or more posts and holes may be used. Additional posts and holes may help disperse loading forces.

It should further be understood that interlocking back guard members 122 with fastening means, such as tabs 141 and recesses 142, may mitigate against extension of spine 10. Also, because back guard members 122 are interlocked, a plurality of back guard members 122 may mitigate against compression of spine 10.

It should be understood that the beginning back guard 122D of a series of back guards, need not have cavities 129. Thus, as shown with a dash line, holes 129 for back guard member 122D are optional.

Also optional are posts 130 for back guard member 122A. Back guard member 122A is the ending member of a plurality. Because back guard 122A is the ending member, posts 134 are optional. In the preferred embodiment, post 134 are omitted for the ending member.

Channel 157 is formed by inner contour 127. Channel 157 is shown by dash lines extending through the plurality of back guard members 122A–122D.

Figure 17:
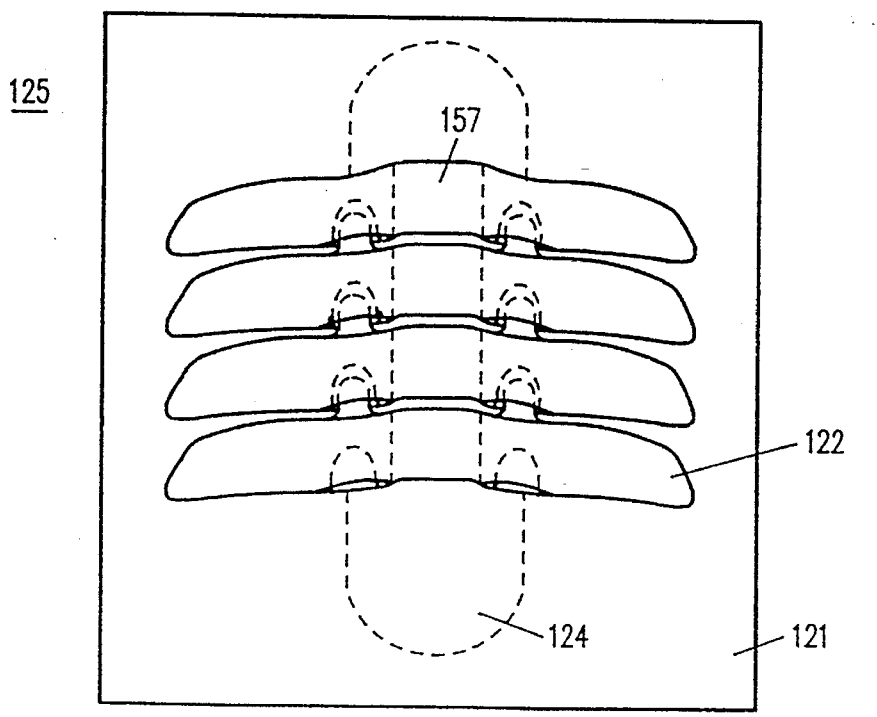
FIG. 17 illustrates a top elevation view of a portion of a back guard according to the present invention.

As shown in FIG. 17, back guard members 122 may be mounted to pad 121. Members 122 may be mounted by riveting, epoxing, or other means well known in the art of the present invention. As shown, channel 124 corresponds to channel 157. Channel 124 is made for disposing channel 157 above channel 124. As can be seen, back guard members interlock at locations disposed apart so as not to interfere with channel 157. Thus, a continuous "tunnel" is provided by channel 157.

Figure 18:
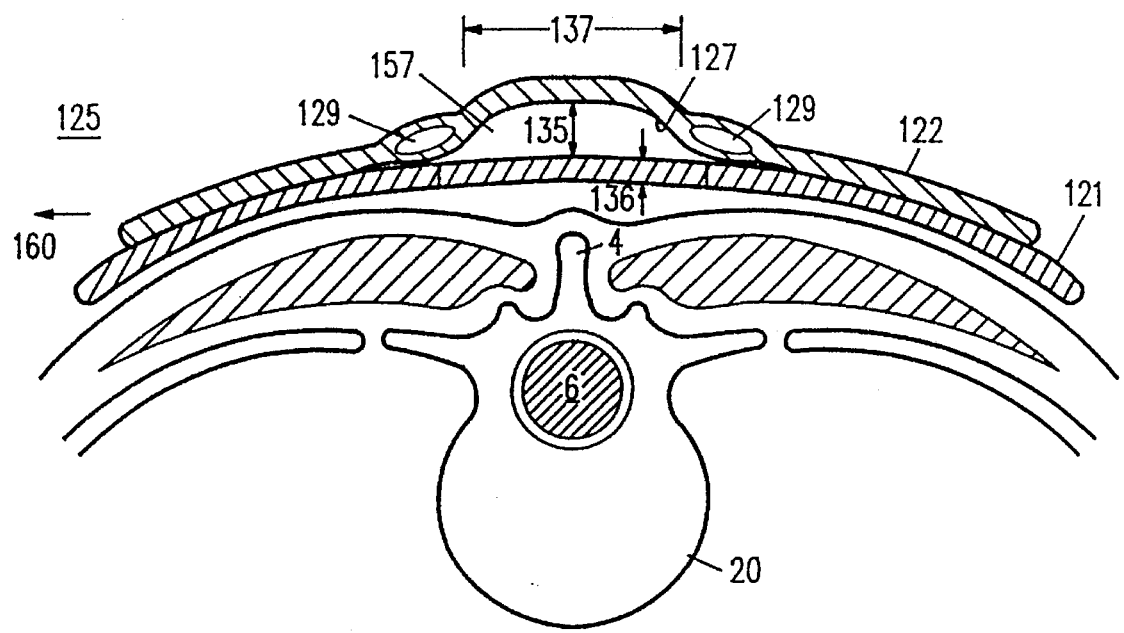
FIG. 18 illustrates a cross-sectional view of a back guard member according to the present invention as applied to the back.

Referring to FIG. 18, a cross section of the back and back guard 125 is shown. As shown, channel 157 comprises a continuous opening. Channel 124 is shown to increase vertical height 135. Height 135 for inner contour 127 is to provide a sufficient recess for the spinous process upon impact. Additionally, width 137 is to provide leeway in case back guard 125 is shifted during impact. Thus, if back guard 125 is moved in a direction 160, there will be some allowable movement which will still provide sufficient recess height 135 for spinous process 4. The amount of recess height 135 will also depend on whether channel 124 is included with pad 121. If channel 124 is included, an additional height 136 increases the overall height 135 to the top of contour 127. In the preferred embodiment of the present invention, height 135 is 3 to 5 centimeters, and width 137 is approximately 7 to 10 centimeters.

Figure 19:
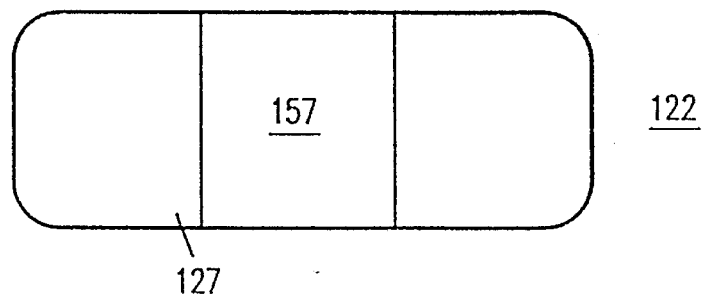
FIG. 19 illustrates a bottom elevation view of a back guard member according to the present invention.

Referring to FIG. 19, an underside of back guard member 122 is shown. As shown, a channel 157 is defined by contour 127.

Figure 20:
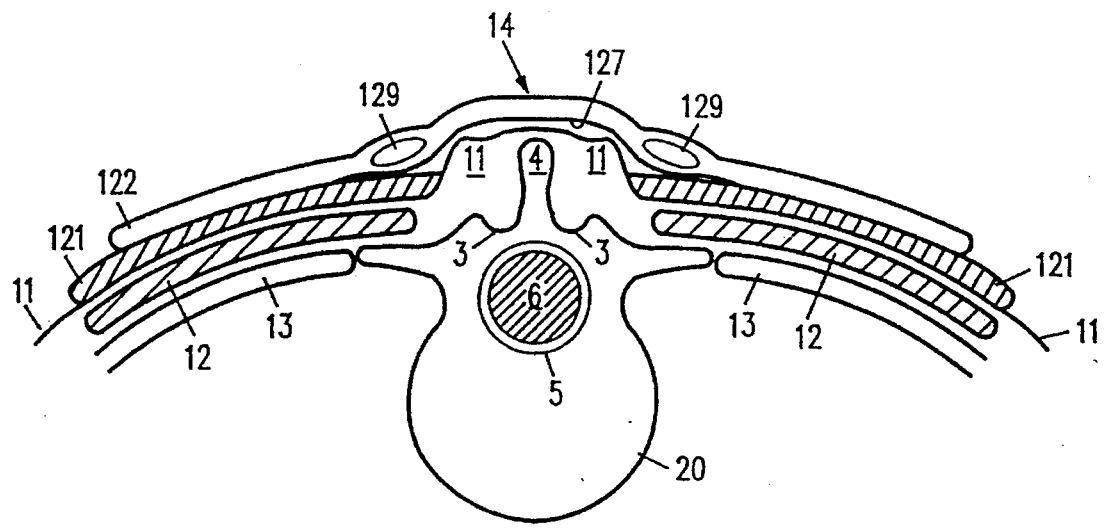
FIG. 20 illustrates how the present invention protects the spinous process from a direct impact.
Figure 21:
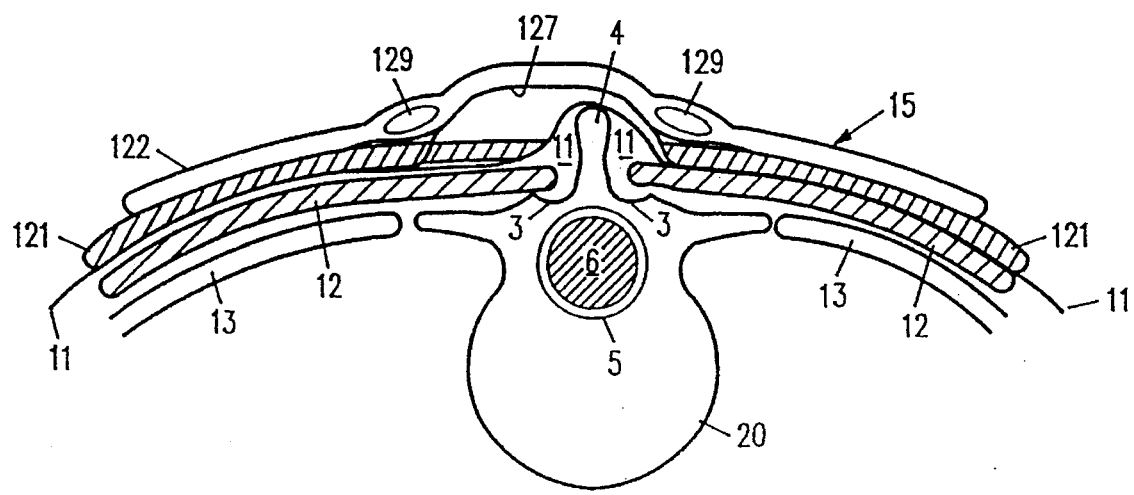
FIG. 21 illustrates how the present invention protects the spinous process from a lateral impact.

Referring to FIGS. 20–21, when a load is delivered to back guard 125, there is a sufficient recess amount to mitigate spinous process 4 from being pushed into spinal cord 6 as described in the above biomechanisms of injury. Thus, if a load 14 is applied to back guard 125 as shown is shown in FIG. 20, the brunt of the force is distributed away from spinous process 4 and onto muscle tissue 12 and ribs 13. Thus, the risk of a severe injury to the back is reduced with back guard 125. Moreover, if a lateral force 15 as shown in FIG. 21 is applied to back guard 25 causing movement thereof, the risk of impact to spinous process 4 is reduced with back guard 125 and most of the force of load 15 is displaced to muscle tissue 12 and ribs 13.

Figure 22:
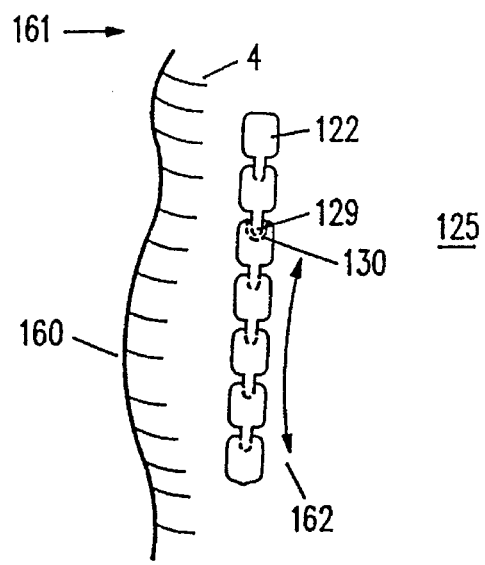
FIG. 22 illustrates how the present invention protects against back strain due to flexion.
Figure 23:
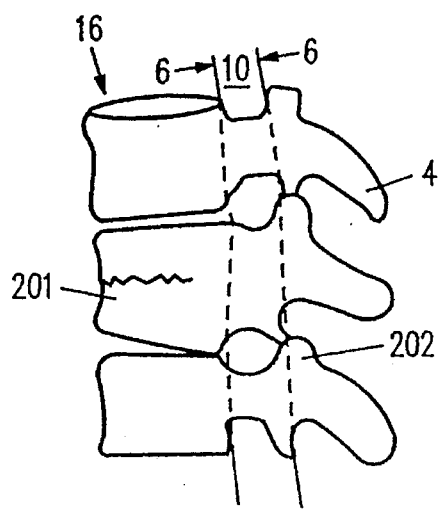
FIG. 23 shows a diagram for illustrating a compression fracture.
Figure 24:
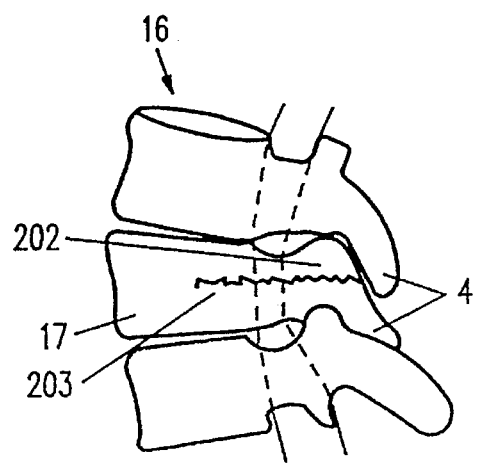
FIG. 24 shows a diagram for illustrating an extension compression fracture.
Figure 26:
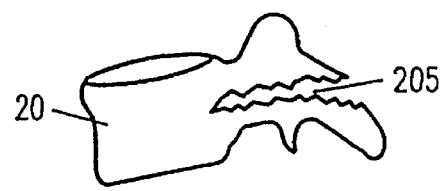
FIG. 26 shows a diagram for illustrating a fracture due to a fraction force.
Figure 25:
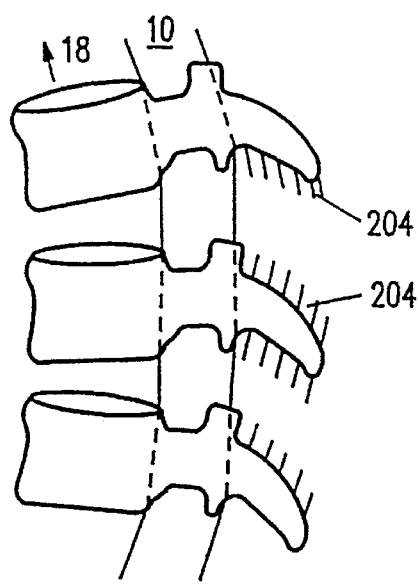
FIG. 25 shows a diagram for illustrating extension of the spinal column.
Figure 27:
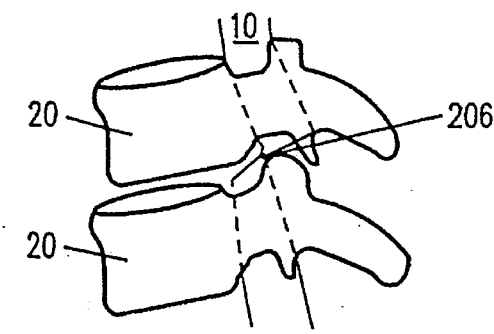
FIG. 27 shows a diagram illustrating misalignment of the spinal column.
Figure 28:
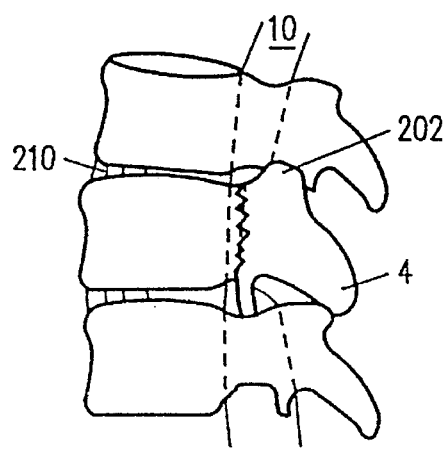
FIG. 28 shows a diagram illustrating injury due extension-compression.

Moreover, as shown in FIG. 22, interlocking back guard members 122 may reduce risk of back strain and hyperextension of the back.

As described above, back guard members 122 are mounted to pad 121. Thus, because posts 130 are contained within holes 129, posts 130 will not only not be pushed into the wearer upon backward flexion, but also will limit backward and forward flexion. As posts 130 may be interlocked into cavities 129, the amount of forward and backward flexion of back guard 125 will be limited by the tolerance between the outer circumference of post 130 as mated with the inner circumference of holes 129. Thus, if back 160 is pushed in a direction 161, arcuate movement 162 of back guard 125 is limited by the mating of post 130 with holes 129 for each back guard member 122. The mating of holes 129 to posts 130 allows for arcuate movement, i.e., normal flexion. However, as some people have more or less flexibility, the amount of allowable arcuate movement may be adjusted accordingly. In the preferred embodiment, backward flexion would be completely eliminated for certain portions of the back, while forward flexion would be limited to 45 degrees.

Also, because posts 130 and holes 129 may be curved for slidable movement during engagement, backward flexion may be limited by a curved shape, e.g., the curved shape shown in FIG. 29. In this manner, the needed difference between outer circumference of post 130 and inner circumference of holes 129 is reduced.

Figure 30:
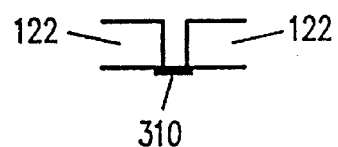
FIG. 30 is a broken-out view of back guard members hinged together in accordance with the present invention.

Because other interlocking means, e.g., hinges 310 attached to members 122 as shown in the broken out view of FIG. 30 or recesses 142 and tabs 141 as shown in FIG. 16, may be used, back guard members 122 need not be mounted to pad 121. Thus, back guard members may exist independently of mounting to fabric. Alternatively, back guard members may be sewn to a jacket or other garment.

Figure 31:
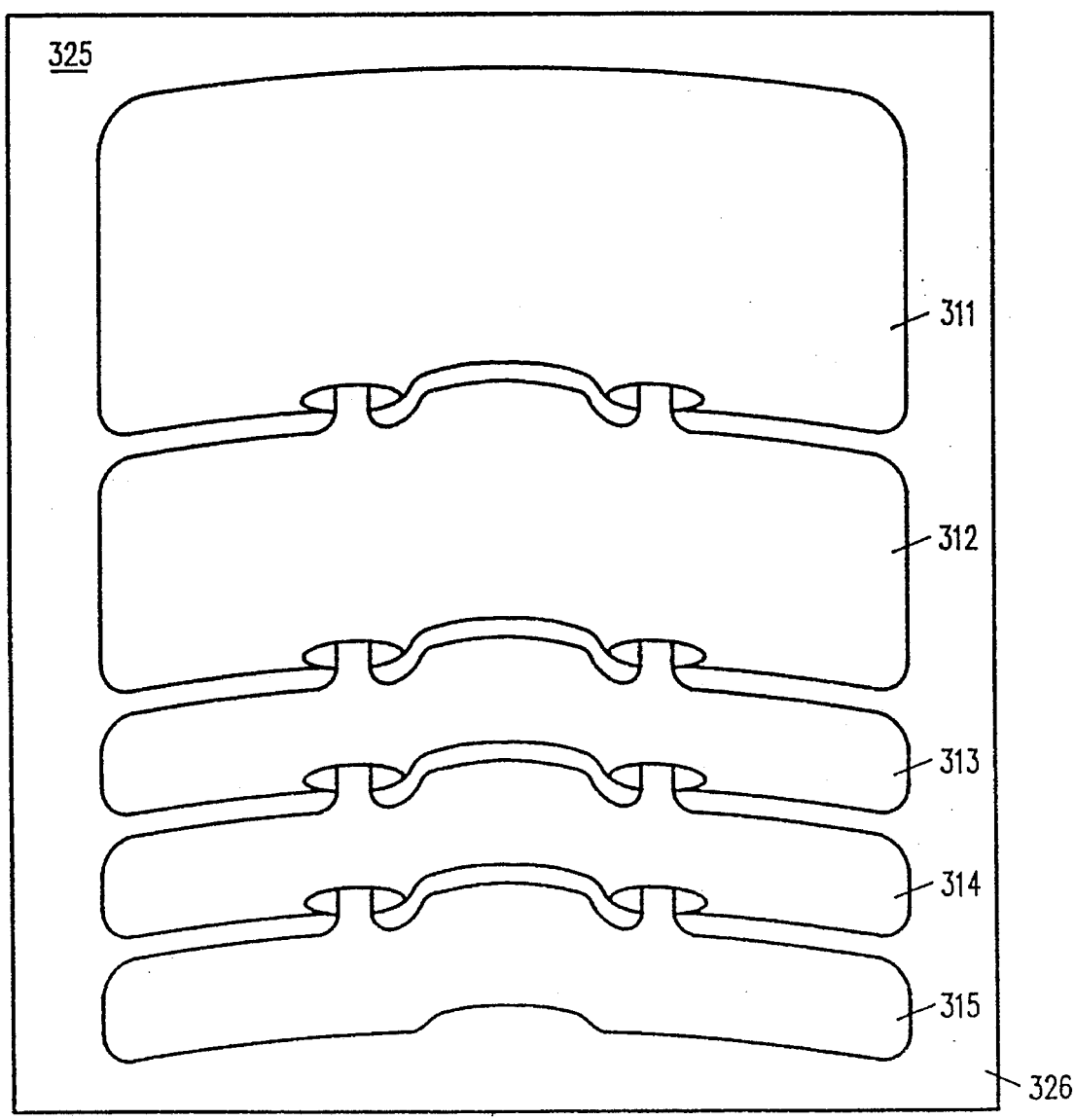
FIG. 31 is a top elevation view of a back guard according to the present invention.

Referring to FIG. 31, back guard 325 is shown attached to garment 326. As shown, back guard 325 comprises back guard members 311–315. Back guard members 311 and 312 are larger than back guard members 313–315. The larger the back guard member, the more reliable dispersion of loading forces will be.

Back guard 325 is designed according to the back's ability to flex. Back guard members 311–312 are for covering thoracic vertebrae. Because thoracic vertebrae do not allow for very much bending by a wearer, fewer and larger back guard members are used for protection of thoracic vertebrae. Back guard members 313–315 are for covering lumbar vertebrae L1–L5. Because lumbar vertebrae do allow for significant bending by a wearer, more and narrower back guard members are used for protection of lumbar vertebrae. Although, protection of lumbar vertebrae may be omitted if only spinal cord protection is desired. Moreover, back guard 325 may be used to protect cervical vertebra C7.

It should be understood that spinal cord 6 does not typically extend the full length of the back. In fact, spinal cord 6 often terminates just below thoracic vertebrae D1–D12. Below where spinal cord 6 terminates, axons extend to couple neurons with synapses. As axons may grow back to re-connect to neurons and synapses, it is not as critical to protect the lower back where the spinal cord does not reside. Therefore, back guard 325 need not extend beyond where spinal cord 6 resides. Additionally, back guard 325 may comprise only one back guard member for protecting a determined region of the back.

Figure 32:
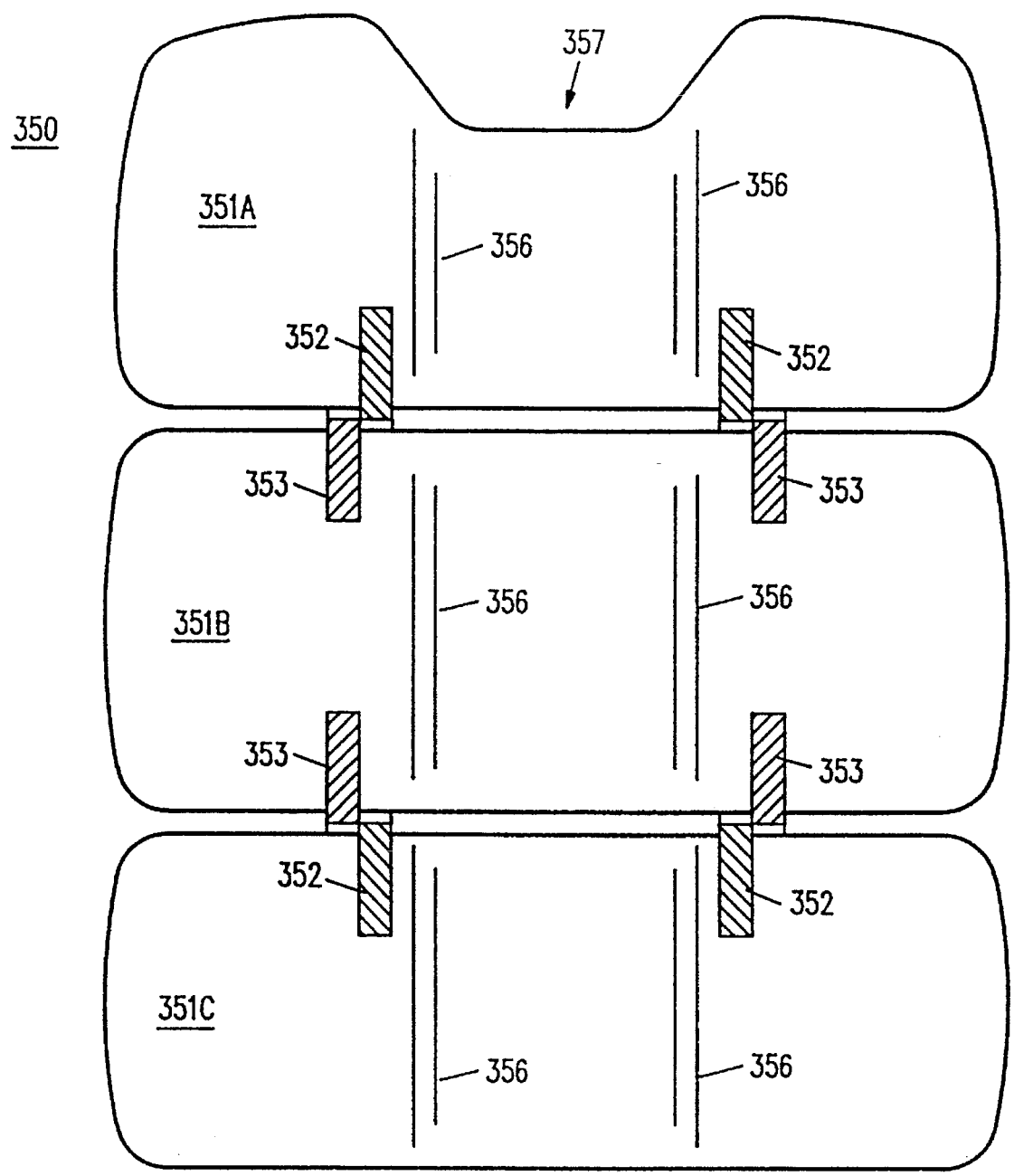
FIG. 32 is a top elevation view of an alternate embodiment of a back guard in accordance with the present invention.

Referring to FIG. 32, there is shown an alternate embodiment of a back guard 350 in accordance with the present invention. Back guard 350 is comprised of a plurality of back guard plates 351A–C. While three plates 351A–C form back guard 350, it should be understood that back guard 350 may be made of fewer or more plates. Plates 351A–C are hinged directly together one to another by straps 352, 353 (shown in FIGS. 33 and 34). Inside straps 352 may alternate with outside straps 353. For example, middle plate 351B comprises four outside straps 353, as opposed to two outside straps 353 and two inside straps 352. However, plates 351A–C need not alternate straps 352, 353 as shown in FIG. 32, and may in fact be applied in some other order.

Plates 351A–C are similar to plates 122 (shown in FIG. 16) in that both are contoured to form a continuous tunnel as indicated by top contour lines 356. The upper most plate 351A may optionally be contoured to accommodate a wearer's neck and/or head, and any movement thereof, by providing a cut-away contour 357.

Again, it should be understood that in order to maintain the integrity of a continuous tunnel upon impact in accordance with the present invention while allowing desired flexibility, back guard plates 351A–C must be mechanically, directly connected individually one to another. While straps are used as one embodiment in accordance with the present invention, it should be understood that other mechanical means may be employed in accordance with the present invention.

Figure 33:
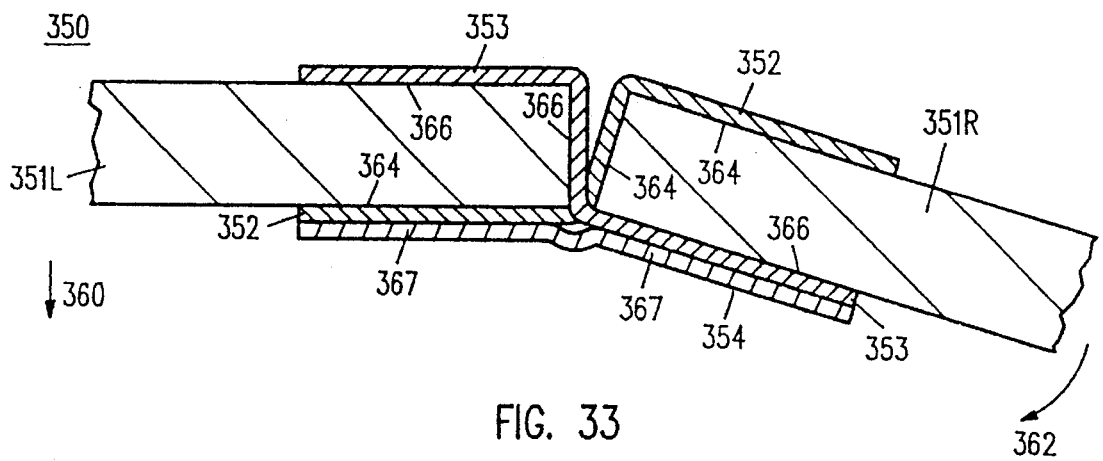
FIGS. 33 and 34 are cross-sections of a portion of the back guard of FIG. 32.

Referring now to FIG. 33, there is shown a side cross-sectional view of a portion of back guard 350. As shown, right plate 351R is turned in an inward direction 362 with respect to left plate 351L. Direction 362 has a component of direction 360, where direction 360 is toward the body of a wearer. Thus, back guard 350 allows a wearer forward bending (flexion) movement.

Figure 34:
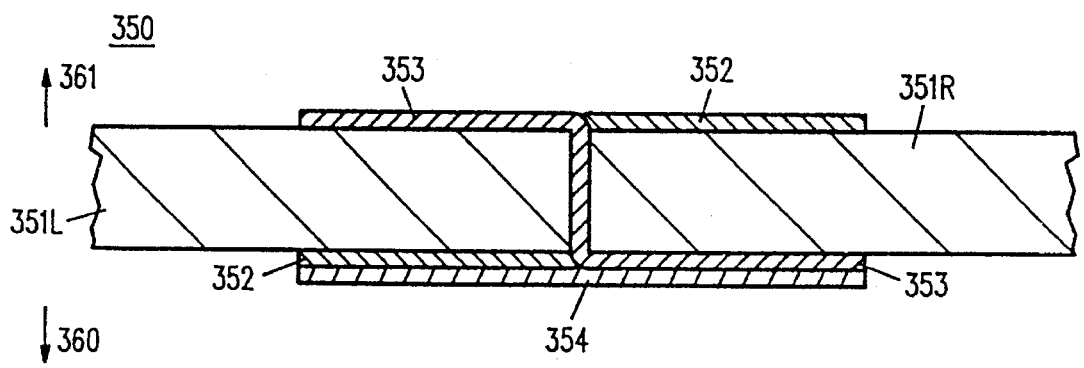

Referring now to FIG. 34, there is shown a side cross-sectional view of a portion of back guard 350 of FIG. 33, except plate 351R is not bent inward. Tension strap 354 prevents bending of back guard 350 in a direction away from the wearer's body, namely, direction 361. Tension straps 354 mitigate to prevent backward flexion to avoid serious back injury.

Figure 35:
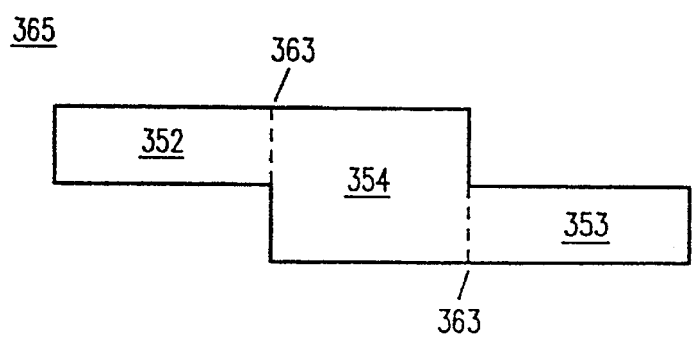
FIG. 35 is a top plan view of an integral strap in accordance with the present invention.

Straps 352, 353 are attached to plates 351A–C via bonding, molding, and the like. Strap 354 is attached to straps 352, 353 via bonding, sewing, and the like. With reference to FIG. 33, straps 352, 353 are attached to plates 351L and 351R along contours 364 and 366. Specifically, strap 352 is attached along contours 364, and strap 352 is attached along contours 366. Strap 354 is attached to both straps 352, 353 at locations 367, namely, the interface of strap 354 to straps 352, 353. Straps 352–354 may be individual straps or may be formed in an integral manner. For example, referring to FIG. 35, an integrally formed fabric hinge 365 is shown. As indicated, tension strap 354 has attached thereto straps 352, 353. Straps 352, 354 are folded over as indicated by fold lines 363. Straps 352, 353 may then be woven between plates 351A–C, shown in FIG. 32, for attachment thereto as previously described. Straps 352, 353 may also be attached to tension strap 354 as previously described.

The materials forming back guard 350, shown in FIG. 32, comprise honey comb aluminum, for plates 351A–C, and kevlar for straps 352–354. Other suitable materials, however, may be employed when practicing the present invention.

The present invention has been particularly shown and described with respect to certain preferred embodiments of features thereof. However, it should be readily apparent to those of ordinary skill in the an that various changes and modifications in form and detail may be made without departing from the spirit and scope of the present invention, and any of them, as set forth in the appended claims. The present invention illustratively disclosed herein may be practiced without any element which is not specifically disclosed herein.

What is claimed is:

1. A back guard comprising:

a plurality of curved plates having inner contours, the plurality of curved plates aligned with one another for forming a continuous tunnel, the continuous tunnel, defined by the inner contours, for corresponding to at least a portion of a human spine, the continuous tunnel having a height along at least a portion thereof of at least 3 cm; and interconnecting means for directly attaching each of the plurality of curved plates one to another for maintaining the continuous tunnel between at least two adjacent ones of the plurality of curved plates.

2. The back guard of claim 1 wherein the two adjacent ones of the plurality of curved plates are directly connected one to another with mechanical means for limiting flexion of the back guard in order to maintain the continuous tunnel.

3. The back guard of claim 2 wherein the mechanical means are straps.

4. The back guard of claim 2 wherein the mechanical means are posts inserted in holes.

5. A back guard for directing forces due to impact away from the spinous processes of a wearer, the back guard comprising:

a plurality of plates; and interlocking means for attaching the plurality of plates one to another, the interlocking means allowing bending movement of the plurality of plates, with respect to each other, toward the wearer while severely limiting bending movement of the plurality of plates, with respect to each other, away from the wearer;

the plurality of plates having inner contours and being aligned with one another for forming a continuous tunnel corresponding to the spinous processes of the wearer, the tunnel providing a height sufficient for receiving heights of the spinous processes of the wearer.

6. The back guard of claim 5 wherein the interlocking means comprises an inner strap, an outer strap, and a tension strap.

7. The back guard of claim 6 wherein the inner strap, the outer strap, and the tension strap are made as one piece of material.

8. The back guard of claim 6 wherein the inner strap and the outer strap are attached between adjacent ones of the plurality of plates, the inner strap and the outer strap being attached in parallel to one another, the tension strap being attached underneath the plurality of plates and to the inner strap and the outer strap.

\* \* \* \* \*